(12) United States Patent
Kohls et al.

(10) Patent No.: US 7,258,665 B2
(45) Date of Patent: Aug. 21, 2007

(54) HIGH AVAILABILITY DEPLOYMENT OF AN OFF-SITE MANAGEMENT SYSTEM FOR DIGITAL CARDIAC ELECTROCARDIOGRAMS OPERATING IN AN APPLICATION SERVICE PROVIDER MODEL

(75) Inventors: Mark R. Kohls, New Berlin, WI (US); Paul J. Herro, Chicago, IL (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 587 days.

(21) Appl. No.: 09/960,792

(22) Filed: Sep. 21, 2001

(65) Prior Publication Data

US 2003/0060689 A1    Mar. 27, 2003

(51) Int. Cl.
*A61B 5/00* (2006.01)
(52) U.S. Cl. .................... 600/300; 128/920
(58) Field of Classification Search ........ 600/300–301, 600/508–509; 128/903, 904, 920, 923
See application file for complete search history.

(56) References Cited

U.S. PATENT DOCUMENTS

| | | | |
|---|---|---|---|
| 5,564,429 A * | 10/1996 | Bornn et al. ............. | 600/301 |
| 5,997,476 A * | 12/1999 | Brown .................... | 600/300 |
| 6,149,585 A * | 11/2000 | Gray ...................... | 600/300 |
| 6,363,462 B1 * | 3/2002 | Bergsten ................. | 711/162 |
| 6,544,173 B2 * | 4/2003 | West et al. .............. | 600/300 |
| 6,709,399 B1 * | 3/2004 | Shen et al. .............. | 128/923 |

* cited by examiner

*Primary Examiner*—Max F. Hindenburg
*Assistant Examiner*—Michael C Astorino
(74) *Attorney, Agent, or Firm*—McAndrews, Held & Malloy, Ltd.; Peter J. Vogel; Michael A. Dellapenna (57) ABSTRACT

A preferred embodiment of the present invention provides a method and system for high availability remote centralized data management. In a preferred embodiment, the system includes a primary remote centralized data storage storing medical data, and a redundant remote centralized data storage storing a redundant copy of the medical data. In a preferred embodiment, the system also includes a primary data server for storing the medical data in the primary remote centralized data storage. In a preferred embodiment, the primary data server also stores the medical data in the redundant remote centralized data storage. Preferably, the system also includes a redundant data server for storing the medical data in the redundant remote centralized data storage and also the primary remote centralized data storage. Additionally, in a preferred embodiment, the system includes an interface allowing access to the system. Preferably, the interface is a redundant interface providing high availability access to the remote centralized data management system.

43 Claims, 3 Drawing Sheets

Figure 1

HIGH AVAILABILITY DEPLOYMENT OF AN OFF-SITE MANAGEMENT SYSTEM FOR DIGITAL CARDIAC ELECTROCARDIOGRAMS OPERATING IN AN APPLICATION SERVICE PROVIDER MODEL

CROSS REFERENCE TO RELATED APPLICATIONS (if applicable)

Not applicable.

STATEMENT REGARDING FEDERALLY SPONSORED RESEARCH & DEVELOPMENT (if applicable)

Not Applicable.

BACKGROUND OF THE INVENTION

The preferred embodiments of the present invention generally relate to electrocardiogram management systems, and in particular relate to a method and system for high availability (HA) deployment of an off-site management system for digital cardiac electrocardiograms (ECGs) operating in an application service provider (ASP) model.

An electrocardiogram (ECG or EKG) is a graphical record of a heart's electrical activity. Typically, ECGs may be obtained as part of routine patient examination. Typically, ECGs may be repeated and updated to maintain a history of a patient's ECGs. An ECG history for a patient may be used to monitor and chart a patient's health and cardiac function.

In order to obtain an ECG, electrodes or electrocardiographic leads may be placed on a patient in areas such as a patient's arms, legs, and chest. ECG readings may be taken on an ECG table. ECG readings may also be obtained with a portable unit. Additionally, ECG data may be recorded using a wearable monitor. Typically, ECGS are recorded electronically. Additionally, ECGs may be charted on paper with an instrument such as a stylus.

The reliable management of ECGs is important to help ensure the availability of ECG information during diagnosis and treatment of a patient. Availability of ECG information is important during diagnosis and treatment of a patient in order to monitor a patient's health and cardiac function. For example, a healthcare practitioner (such as a physician, nurse, assistant, technician, or other medical professional, for example) may use trends in ECG patterns to diagnose a cardiac condition in a patient. Additionally, awareness of a cardiac condition in a patient may affect the course of treatment prescribed by the healthcare practitioner.

Quality and reliability often translate into success in the medical device marketplace. For example, an ECG management system may serve more than thirty customers. A failure in the ECG management system may result in dissatisfaction with the ECG management system and with a company's services. Customer dissatisfaction may affect future business opportunities for the company. Thus, there is a need to reduce errors and failures in ECG management systems to provide quality service. Additionally, there is a need for an ECG management system designed with high availability to improve ECG management system up-time and availability of information for medical diagnosis and treatment.

Currently, a service technician is typically dispatched to a customer site in the event of an ECG management system failure. Often, service calls by a service technician to a customer site may be expensive and time-consuming due to the location of the customer site, the nature of the problem, and the timing of the call. Thus, there is a need for redundant, high availability systems to reduce the dispatch of service technicians to a customer site. A reduction in service calls may reduce the amounts paid for service support, especially during expensive periods such as holidays, weekends, or nights.

A highly available or high availability system is defined in the art as a system that provides reliable access, such as through redundant systems and redundant storage to help ensure reliable storage and retrieval of data and services, for example. A highly available system design may improve operation of an ECG management system for operations of a customer such as a healthcare facility (such as a hospital, clinic, doctor's office, or other medical office, for example) through reliable storage and retrieval of ECGs. For example, a reliable ECG management system allows ECG data to be available for use by a cardiologist or other user in treatment and diagnosis by helping to prevent system failures and system downtime. Availability of data helps allow a cardiologist or other such user to read and diagnose cardiac complications quickly. Thus, prompt access to data and diagnosis of the data help allow a cardiologist to provide a high level of care to a patient.

Additionally, remote, centralized access to ECG data may allow multiple users to reliably access ECG data. Centralized ECG storage may allow computing resources and support to be pooled in a smaller number of locations. In the field of computers, Application Service Providers (ASPs) have been employed to allow for centralized access and storage of data. ASPs operate as hosts for data and applications. Typically, ASPs maintain applications and data in an off-site data center. ASPs have been hired by companies in the field of computers to manage data and computer applications. Companies may access data and applications via an ASP. Typically, in the computer field, companies remotely access data and applications via an ASP central data location.

In the field of computers, ASPs may offer several desirable services, such as secure data storage, data backup, and redundant systems. Because ASPs offer such services, a customer of an ASP may not have to incur additional expenses for its own security, backup, and storage systems. In addition to functioning as a remote database, ASPs may host a number of applications that may be activated or accessed remotely by customers. By concentrating computing power and maintenance at the ASP, the ASP may offer continuous access to and support of the applications and alleviate the need for the customer to purchase and maintain its own expensive computer equipment. For example, ASPs may provide installation, management, and support of applications and storage of data for many remote clients. Client data may be stored at a remote data center. Data may be retrieved from a remote data center via a communications medium such as the Internet or a private network.

There is a need in the medical field for centralized remote access to ECG data for use in the diagnosis and treatment of patients. There is also a need for reliable access to ECG data to help ensure that the ECG data may be used by healthcare practitioners in diagnosis and treatment of patients. There is a further need for a highly available ECG management system to support reliable access to ECG data.

Thus, there is a need in the medical field for a remote, centralized, reliable, high availability ECG management system to help ensure access by healthcare practitioners to ECG data to support diagnosis and treatment of patients. Central, remote maintenance may reduce the resources employed at healthcare facilities by reducing manual transfer of ECG data between healthcare facilities and by reducing resources for the maintenance of ECG data at healthcare facilities. Redundant, high availability systems may improve reliability of access to ECG data by healthcare practitioners for diagnosis and treatment of patients by reducing system failures. Thus, a need exists for a method and system for high availability deployment of an off-site management system for digital cardiac electrocardiograms operating in an application service provider model.

BRIEF SUMMARY OF THE INVENTION

A preferred embodiment of the present invention provides a method and system for high availability remote centralized data management. In a preferred embodiment, the system includes a primary remote centralized data storage storing medical data, and a redundant remote centralized data storage storing a redundant copy of the medical data. In a preferred embodiment, the system also includes a primary data server for storing the medical data in the primary remote centralized data storage. In a preferred embodiment, the primary data server also stores the medical data in the redundant remote centralized data storage. Preferably, the system also includes a redundant data server for storing the medical data in the redundant remote centralized data storage and also the primary remote centralized data storage. Additionally, in a preferred embodiment, the system includes an interface allowing access to the system. Preferably, the interface is a redundant interface providing high availability access to the remote centralized data management system. In a preferred embodiment, the system also includes a data source, such as an electrocardiogram unit, for generating medical data, such as electrocardiogram or waveform data, demographic data, measurements, and interpretations of signal data. Also, the system may include an authentication unit for authenticating access to the high availability remote centralized data management system.

In a preferred embodiment, the method includes receiving the medical data and storing the medical data in a remotely accessible centralized data storage. Additionally, the method includes authenticating access to the remotely accessible centralized data storage. In a preferred embodiment, the method also includes storing the medical data in a redundant data storage, preferably using a remote data server. Additionally, the method preferably includes retrieving the medical data from the remotely accessible centralized data storage, preferably using the remote data server.

DETAILED DESCRIPTION OF THE INVENTION

The preferred embodiments of the present invention provide a high availability system for storing and retrieving waveform data, demographic data, measurements, and interpretations of signal data. The preferred embodiments provide redundant access to the high availability system. Additionally, the preferred embodiments provide redundant data storage at the high availability system.

Figure 1:
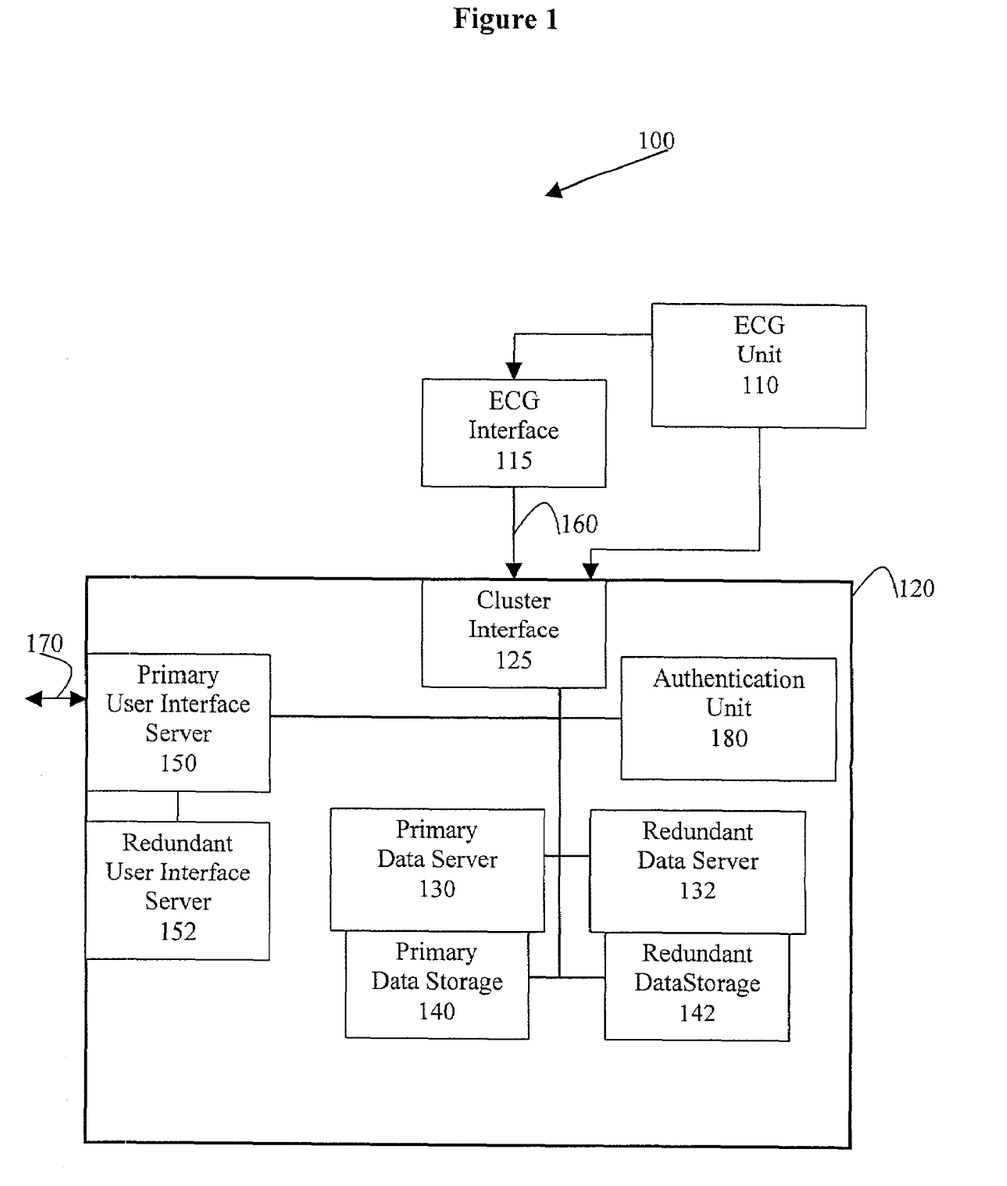
FIG. 1 illustrates an ECG management system used in accordance with a preferred embodiment of the present invention.

FIG. 1 illustrates an ECG management system 100 used in accordance with a preferred embodiment of the present invention. The ECG management system 100 includes a plurality of subsystems, such as an ECG unit 110, a database server cluster 120, an ECG connection 160, and a user connection 170. The ECG unit 110 includes an ECG interface 115. The ECG connection 160 connects the ECG unit 110 to the database server cluster 120. The database server cluster 120 includes a cluster interface 125, primary data server 130, redundant data server 132, primary data storage 140, redundant data storage 142, and primary user interface server 150, redundant user server 152. The user connection 170 allows a user to access the database server cluster 120. The system 100 may also include an authentication unit 180.

In a preferred embodiment, the ECG unit 110 may be used to obtain ECG data from a patient. The ECG unit 110 may also be used to store the ECG data at the database server cluster 120 or other external database. Preferably, the ECG unit 110 is a portable device such as a cart. Alternatively, the ECG unit 110 may be an examination table. Preferably, a patient is connected to the ECG unit 110 to monitor the patient's cardiac activity and ECG data. Then, an operator may use the ECG unit 110 to store and/or analyze the ECG data. In a preferred embodiment, the operator of the ECG unit 110 selects the information to be stored at the database server cluster 120. In an alternative embodiment, the ECG unit 110 automatically stores the information for a patient to the database server cluster 120. In an alternative embodiment, the ECG unit 110 may be a data source used to obtain medical data, such as examination data, images, stress test data, electroencephalogram (BEG) data, electromyogram (EMG) data, or other waveform data, demographic data, measurements, and interpretations of signal data, for example. For illustration purposes, the example of medical data used throughout the description is ECG or other waveform data.

Preferably, the ECG interface 115 facilitates communication between the ECG unit 110 and the database server cluster 120 via the ECG connection 160. Preferably, the ECG interface 115 allows the ECG unit 110 to transmit ECG data or other waveform data to the database server cluster 120 for storage. Alternatively, the ECG interface 115 may allow the database server cluster 120 to transmit information to the ECG unit 110 or from the ECG unit 110. In a preferred embodiment, the ECG interface 115 includes at least one modem to access a plurality of phone lines to call the database server cluster 120 via the ECG connection 160. For example, the ECG interface 115 may include eight modems to access eight different phone lines into the database server cluster 120. Alternatively, the ECG interface 115 may comprise at least one Ethernet adaptor, Internet adaptor, wireless transmitter, cable, and/or other such access device, for example. Preferably, the ECG interface 115 is a redundant system with multiple access devices to provide high availability.

Preferably the ECG connection 160 is at least one phone line. Alternatively, the ECG connection 160 may be at least one Ethernet connection, Internet connection, wireless connection, direct cable connection, Bluetooth, and/or other such connection, for example. Preferably, the ECG connection 160 is a redundant system that allows transfer of data between the ECG interface 115 of the ECG unit 110 and the cluster interface 125 of the database server cluster 120. In a preferred embodiment, data is transmitted using a secure client/server protocol.

In a preferred embodiment, the database server cluster 120 stores ECG data and other waveform data, demographic data, measurements, and interpretations of signal data and provides access to the ECG data and other waveform data. Preferably, the database server cluster 120 is a high availability system with redundant components. Preferably, the database server cluster 120 is an application service provider. The location of the database server cluster 120 in relation to the ECG unit 110 is not fixed and does not affect the operation of the system 100. In a preferred embodiment, the database server cluster 120 includes a primary data server 130 and a redundant data server 132. Preferably, all data servers 130, 132 in the database server cluster 120 include up-to-date applications, databases, and/or operating systems, for example. In the event of a failure in the primary data server 130, the redundant data server 132 automatically takes over operation.

In a preferred embodiment, the data servers 130, 132 store ECG data and/or other data (such as waveform data, demographic data, measurements, and interpretations of signal data.), for example. Alternatively, the data servers 130, 132 may also store applications or programs, such as scheduling programs, medical diagnostic programs, or educational programs, for example. Preferably, the data servers 130, 132 are redundant systems including redundant power supplies, redundant cooling fans, and/or RAID (Redundant Array of Independent Disks) drives for operating systems, applications, and/or data to protect against disk failure, system failure, and/or data corruption, for example. Preferably, the ECG unit 110 may access the data servers 130, 132 at the database server cluster 120 to store ECG or other waveform data, for example. Additionally, a user may access the data servers 130, 132 at the database server cluster 120 to store, retrieve, and/or distribute ECG or other waveform data, for example.

Preferably, the primary data server 130 includes primary data storage 140. Additionally, the redundant data server 132 preferably includes redundant data storage 142. The data storage 140, 142 store data, such as ECG data and/or other waveform data, demographic data, measurements, and interpretations of signal data., for example, in a database or other data storage arrangement, for example. Preferably, the data storage 140, 142 include a redundant hard disk drive array. Preferably, the hard disk drive arrays of the data storage 140, 142 are deployed in RAID (Redundant Array of Independent Disks) format. Using RAID, information may be distributed among a plurality of disks to provide a fast and reliable data storage system and protect against disk failure. Preferably, the primary data storage 140 includes a primary disk, a redundant disk that is ready for use in the event of primary disk failure, and another disk that is available for data parity. Preferably, the redundant data storage 140 is configured in a manner similar to the primary data storage 140. In a preferred embodiment, the primary data server 130 may access the primary data storage 140 and the redundant data storage 142. Additionally, the redundant data server 132 may preferably access the redundant data storage 142 and the primary data storage 140.

In a preferred embodiment, the cluster interface 125 allows the ECG unit 110 to communicate with the database server cluster 120 via the ECG connection 160. The cluster interface 125 communicates with the ECG interface 115 to allow the exchange of data between the ECG unit 110 and the database server cluster 120. Preferably, the cluster interface 125 is connected to the data servers 130, 132. Preferably, the cluster interface 125 includes a plurality of redundant communications devices, such as modems or other network access cards, for example, to receive data from the ECG unit 110 or other data source, for example. Preferably, the multiple communications devices operate on a single bus. For example, the cluster interface 125 may include a bank of eight modems that operate on a single bus to receive data from the ECG unit 110.

Preferably, the user interface servers 150, 152 allow users to access the database server cluster 120. That is, a user may access the database server cluster 120 at the primary user interface server 150 or redundant user interface server 152 via the user connection 170. Preferably, a user may access the user interface server 130, 132 using a web browser, a GE Medical Systems' MUSE CV™ workstation, a PACS (Picture Archiving and Communications System), a terminal, or other such access device, for example. The user interface servers 150, 152 may be web servers allowing access to data in the data storage 140, 142 of the data servers 130, 132. Preferably, the user interface servers 150, 152 are redundant user interface servers. That is, the user interface servers 150, 152 include current applications, databases, and operating systems to provide high availability, reliable access to the database server cluster 120. In the event of a failure in the primary user interface server 150, the redundant user interface server 152 assumes control over access operations automatically. Preferably, the user interface servers 150, 152 also include redundant power supplies, redundant cooling fans, redundant network interface cards (e.g. fast Ethernet), and/or RAID drives for operating systems, applications, and/or data to protect against disk failure, system failure, and/or data corruption, for example.

Preferably, the user connection 170 allows users to communicate with the database server cluster 120. In a preferred embodiment, the user connection 170 is the Internet, a private network, Ethernet, phone line, or other such connection, for example. Preferably, the user connection 170 is a redundant system including redundant components such as redundant network cables, switches, and/or routers used to transmit data to a network such as the Internet or a private network, for example. In the event of a failure in a user connection 170 component, the corresponding redundant user connection 170 component will handle network traffic.

In an alternative embodiment, the cluster interface 125 may be integrated with the user interface servers 150, 152 to allow access by the ECG unit 110 and other users. In an alternative embodiment, the ECG connection 160 and the user connection 170 may be the same connection allowing bi-directional communication between the database server cluster 120 and an external user, such as the ECG unit 110, a physician, a technician, or another user, for example. While the above embodiments are representative of the present invention, the system 100 may include a plurality of the subsystems described above.

In an alternative embodiment, the database server cluster may include an authentication unit 180 to authenticate access to the database server cluster via the cluster interface 125 and/or the user interface servers 150, 152. Preferably, the authentication unit 180 includes a predetermined authentication code or set of authentication codes (such as a database or table of codes, for example). For example, the authentication unit 180 preferably includes an authentication code. The authentication code may be generated in any of a number of ways, including user input, daily generation, monthly generation, random generation, and/or other such method of generation, for example. The authentication unit

180 may receive an authentication code, such as a password, identification number, or other authentication code, for example, from the ECG unit 110 at the cluster interface 125 and/or another user at the user interface servers 150, 152, for example. Preferably, the authentication code may be assigned according to an individual user, a group of users, a type of data source, a location, and/or a function, for example. In a preferred embodiment, the authentication unit 180 includes redundant components to help ensure reliability.

The ECG unit 110 is connected to the database server cluster 120 via the ECG connection 160. The ECG unit 110 and the database server cluster 120 communicate through the ECG interface 115 and the cluster interface 125 via the ECG connection 160. A user connects to the database server cluster 120 at the user interface server 150, 152 via the user connection 170. Within the database server cluster 120, the cluster interface 125 and the user interface servers 150, 152 are connected to the data servers 130, 132. Data from the data storage 140, 142 may be accessed through either of the data servers 130, 132.

In operation, an ECG or other waveform data, for example, is obtained from a patient using the ECG unit 110 and stored at the ECG unit 110. For example, a patient is hooked up to an ECG cart at a hospital. Then, for example, an ECG is electronically charted from the electrical function of the patient's heart. Then, for example, the ECG of the patient is stored in the memory of the ECG cart.

Next, the ECG unit 110 connects to the database server cluster 120 via the ECG connection 160 using the ECG interface 115. For example, one of the on-board modems of the ECG cart dials in to the database server cluster 120 via a phone line. The ECG interface 115 connects to the cluster interface 125 via the ECG connection 160. For example, one of the modems of the ECG cart establishes a phone connection with one of the receiving modems at the database server cluster 120. The ECG interface 115 may be manually connected to the ECG connection 160 (for example, plugging the phone line into the modem). Alternatively, the ECG interface 115 may be continually connected to the ECG connection 160 (for example, a dedicated connection at the ECG table). Additionally, the ECG interface 115 may not have a physical connection to the ECG connection 160 (for example, a wireless connection). Preferably, if one of the components at the ECG interface 115 and/or cluster interface 125 fails, a redundant component is available to perform the requested functionality. For example, if one of the ECG cart modems fails, another modem in the ECG modem bank takes over and dials the modem bank of the database server cluster 120.

Then, access to the database server cluster 120 may be authenticated by the authentication unit 180. That is, the cluster interface 125 may prompt the ECG unit 110 (preferably, the user at the ECG unit 110) for an authentication code, which is described above. For example, upon establishing a modem connection, the user at the ECG cart is prompted to enter a password for access to the database server cluster 120. Next, the ECG unit 110 transmits the authentication code to the authentication unit 180 via the cluster interface 125. Then, the authentication unit 180 compares the received authentication code to the predetermined authentication code, which is discussed above. If the authentication code does not match the predetermined authentication code, then access to the database server cluster 120 is not allowed. Alternatively, another attempt may be made to enter an authentication code. If the authentication code matches the predetermined authentication code, then access to the database server cluster 120 is allowed. For example, the authentication unit 180 compares the user's password against the list of passwords stored in the authentication unit 180 and finds a match. Thus, for example, the user at the ECG cart may access the database server cluster 120.

The ECG unit 110 may then access the database server cluster 120. That is, the ECG unit 110 may access the data server 130 via the ECG interface 115 and the cluster interface 125. For example, the ECG cart accesses the data server 130 of the database server cluster 120 to store the ECG of the patient.

Finally, the ECG unit 110 may store the ECG at the primary data storage 140 via the primary data server 130. For example, the user at the ECG cart transfers the ECG to the primary data server 130, and the primary data server 130 stores the ECG in a RAID drive. After the ECG is stored at the primary data storage 140, the primary data server 130 preferably archives the ECG at the redundant data storage 142 via the redundant data server 132. For example, after the ECG of the patient is stored in the RAID drive, the primary data server 130 copies the ECG and sends the copy of the ECG to the redundant data server 132. Then, for example, the redundant data server 132 stores the ECG of the patient at a backup disk. Thus, for example, a primary copy of the ECG and a redundant archive copy of the ECG are stored in the database server cluster 120.

Once the ECG has been stored, the data servers 130, 132 and the data storage 140, 142 are updated to reflect the presence of the ECG. For example, the ECG file is added to the directories of the data servers 130, 132 so that the ECG may be found at the RAID drive and backup disk. Additionally, the update may be reflected at the user interface servers 150, 152 to enable users to access the ECG via the user interface servers 150, 152, as discussed below. For example, the web server of the database server cluster 120 is updated to add a link to the ECG.

Alternatively, if the primary data server 130 and/or the primary data storage 140 have an error and/or failure, for example, the ECG may be stored at the redundant data storage 142 via the redundant data server 132. For example, when the ECG cart attempts to store the ECG at the RAID drive via the primary data server 130, the primary data server 130 is unavailable due to hardware failure. Thus, for example, the ECG cart transfers the ECG to the redundant data server 132 for storage at the RAID drive or the backup disk.

Later, a user may access an ECG at the database server cluster 120. The user may use a web browser, a GE Medical Systems MUSE CV™ workstation graphical user interface, or other such information access device, for example. For example, the patient returns to the hospital and a new ECG is obtained. The doctor, for example, wishes to examine the stored ECG of the patient to compare the stored ECG of the patient to the newly obtained ECG of the patient. Preferably, the user may connect to the primary user interface server 150 via the user connection 170 using the web browser, GE Medical Systems MUSE CV™ workstation graphical user interface, or other such information access device, for example. For example, the doctor may use a web browser on a personal computer to connect to the web server of the database server cluster 120 via the Internet.

Next, access to the database server cluster 120 may be authenticated using the authentication unit 180. Access may be authenticated using an authentication code as described above. For example, the doctor is prompted for a password at the web browser, and the password that the doctor enters is compared to a table of passwords stored at the authentication unit 180. When the authentication unit 180 matches the doctor's password to an entry in the password table, for example, the doctor is allowed to access the database server cluster 120 via the web server.

Then, the user may request the ECG or other waveform data, demographic data, measurements, and interpretations of signal data., for example, from the data server 130 via the primary user interface 150. For example, the doctor selects the link at the web server to the ECG file. Next, the primary user interface 150 transmits the request to the primary data server 130. For example, the web server requests the ECG from the primary data server 130. Then, the primary data server 130 retrieves the ECG from the primary data storage 140. For example, the primary data server 130 locates the ECG file in the directory of the RAID drive and retrieves the ECG file from the RAID drive. Next, the primary data server 130 transmits the ECG to the primary user interface server 150. For example, the primary data server 130 transfers the ECG to the cache of the web server. Finally, user may view the ECG or other waveform data, demographic data, measurements, and interpretations of signal data, at the primary user interface server 150 via the web browser, GE Medical Systems MUSE CV™ workstation graphical user interface, or other such information access device, for example. For example, the doctor may view the stored ECG of the patient at the web server via the web browser on the personal computer.

Alternatively, if the primary user interface server 150 has an error or a failure, for example, the user may access the redundant user interface server 152. Additionally, if the primary data server 130 has an error or a failure, for example, the user interface servers 150, 152 may access the redundant data server 132. Furthermore, if the primary data storage 140 has an error or a failure, for example, the data servers 130, 132 may access the redundant data storage 142 and retrieve the ECG or other waveform data, for example.

Additionally, a user may store an ECG or other waveform data, for example, at the database server cluster 120 via the user interface servers 150, 152. For example, the doctor may store the newly obtained ECG of the patient at the database server cluster 120 via the primary user interface server 150. First, the user may access the database server cluster 120 via the primary user interface server 150 as described above. For example, the doctor accesses the database server cluster 120 via the Internet using a web browser. Then, the user may be authenticated by the authentication unit 180 as described above. For example, the doctor's password is verified and access is granted.

Next, the user may transmit the ECG or waveform to the primary user interface server 150 via the user connection 170. For example, the doctor initiates an FTP (File Transfer Protocol) session to the web server via the web browser, and transfers an electronic stored copy of the new ECG to the web server via the ftp session. Then, the primary user interface server 150 transfers the ECG or waveform to the primary data server 130. For example, the web server transmits the new ECG to the primary data server 130 for storage with the old ECG file. Next, the primary data server 130 stores the ECG or waveform at the primary data storage 140 as described above. For example, the primary data server 130 stores the new ECG in the RAID drive. Then, the stored ECG or other waveform is duplicated in the redundant data storage 142, as described above. Finally, as described above, the contents (for example, the directory) of the data servers 130, 132 and the user interface servers 150, 152 are updated to reflect the presence of the ECG or other waveform, for example. Preferably, as described above, if a problem arises with the primary user interface server 150, the primary data server 130, and/or the primary data storage 140, for example, the redundant user interface server 152, redundant data server 132, and/or redundant data storage 142, for example, may be used.

Figure 2:
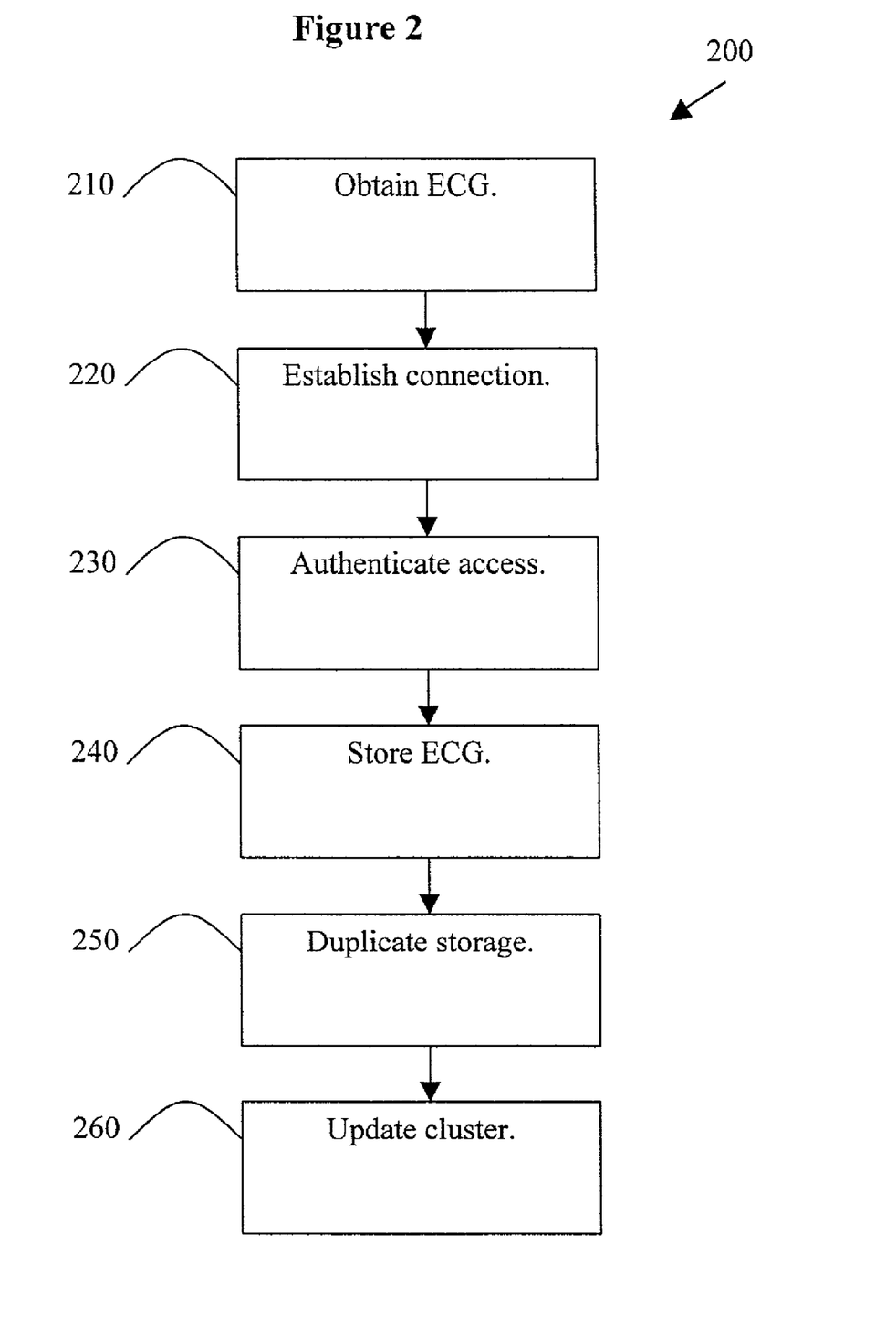
FIG. 2 illustrates a flowchart for high availability ECG storage used in accordance with a preferred embodiment of the present invention.

FIG. 2 illustrates a flowchart 200 for high availability ECG storage used in accordance with a preferred embodiment of the present invention. First, at step 210, an ECG or other waveform data, demographic data, measurements, and interpretations of signal data, for example, is obtained from a patient. The ECG or other waveform data may be stored locally. For example, an ECG is obtained from a patient connected to an ECG table at a hospital.

Next, at step 220, a connection is established with a remote, high availability database server cluster. For example, one of a bank of modems in the ECG table dials in to one of a bank of modems at the database server cluster. If one of the bank of modems fails, for example, another modem in the bank of modems may complete the connection.

Then, at step 230, access to the database server cluster may be authenticated. For example, upon establishing a modem connection, a user at the ECG table is prompted for a password or other authentication code for access to the database server cluster. The authentication code is compared to a predetermined authentication code, which is discussed above. If the authentication code does not match the predetermined authentication code, then access to the database server cluster is not allowed. Alternatively, another attempt may be made to enter an authentication code. If the authentication code matches the predetermined authentication code, then access to the database server cluster is allowed. For example, the user's password is compared against a list of preset passwords. If, for example, the user's password matches a password in the list, access to the database server cluster is allowed.

Next, at step 240, the ECG or other waveform may be stored at the database server cluster. For example, the user at the ECG table transmits the ECG to the database server cluster for storage in a redundant storage device, such as a RAID drive, for example. Preferably, the ECG or other waveform data is stored in a redundant storage system to provide reliable, high availability storage.

Then, at step 250, the stored ECG or other waveform data is preferably duplicated at a secondary, redundant storage. For example, the stored ECG is copied from the RAID drive to a backup hard disk array. Redundant systems and redundant data help ensure that the database server cluster is a reliable, high availability system for ECG storage and management.

Finally, at step 260, the database server cluster is updated to reflect the storage of the ECG or other waveform data. That is, the name and location of the ECG or waveform file are added to the interfaces and/or directory structures of the database server to enable location and retrieval of the ECG or other waveform data, demographic data, measurements, and interpretations of signal data. For example, after the ECG is stored, the name and location of the ECG file are added to the database server cluster directory and the web server of the database server cluster is updated to reflect a link to the ECG file.

Additionally, an ECG or other waveform data may be stored at the remote, high availability database server cluster as described above using a web browser, a GE Medical Systems MUSE CV™ workstation graphical user interface, or other such information access device, for example, and a web server or other such user interface server, for example. The web browser, GE Medical Systems MUSE CV™ workstation graphical user interface, or other such information access device may access the web server or other such user interface server at the database server cluster and transfer the ECG or other waveform data to the database server cluster via the web server or other such user interface server, for example. The ECG or other waveform data is then redundantly stored at the database server cluster as described above.

For example, a doctor may obtain an ECG of a patient at a hospital and store the ECG on a local MUSE CV™ workstation. Then, the doctor may access the user interface server 150 of the database server cluster using a graphical user interface on the MUSE CV™ workstation. After authentication of the access, the doctor may transmit the ECG to the user interface server 150, such as by dragging the icon of the ECG on the local drive to the directory of the user interface server 150. Then, the user interface server 150 transfers the ECG to the redundant storage of the database server archive. Finally, the user interface server 150 is updated to add a link to the ECG file at the database server archive.

Figure 3:
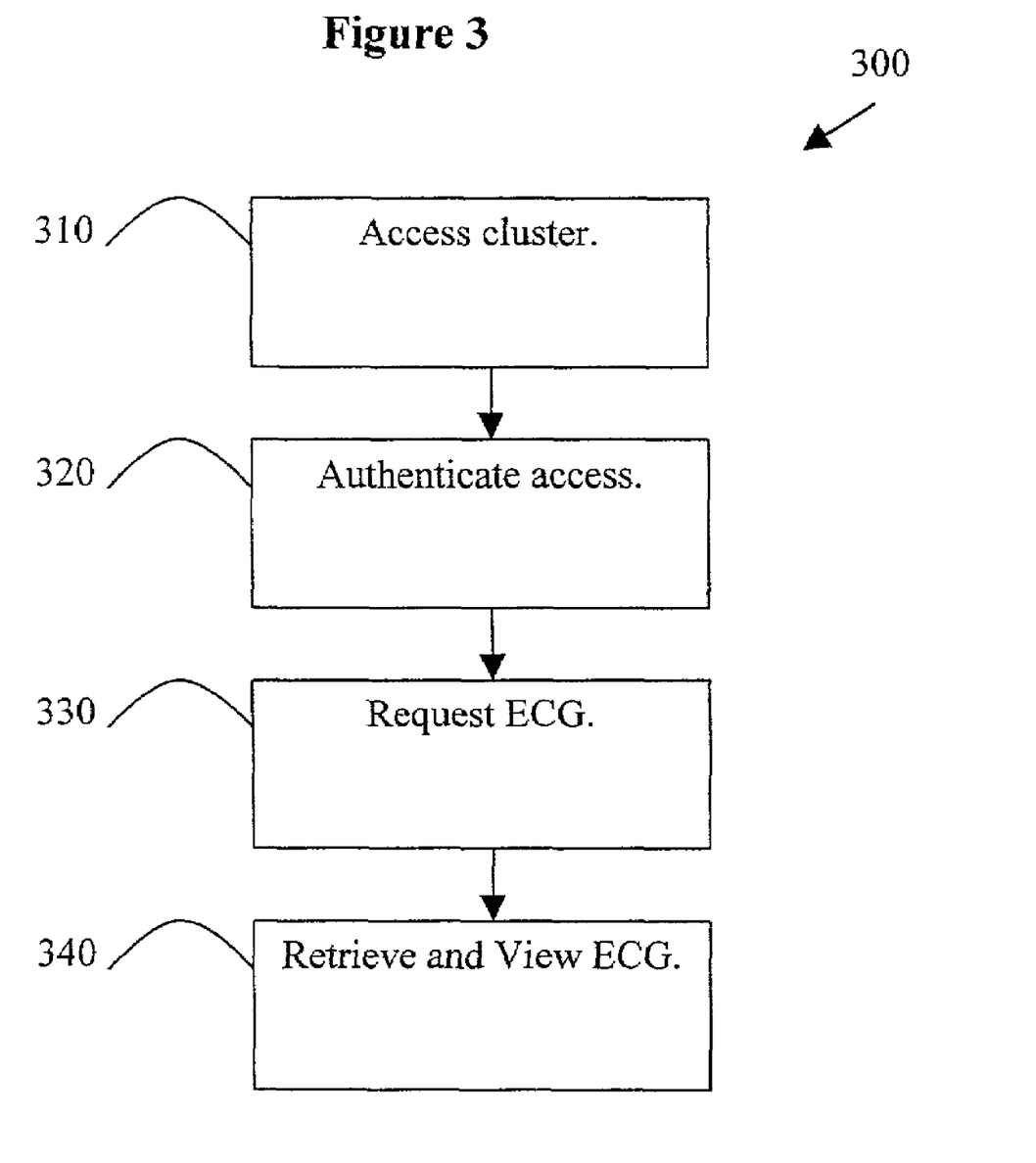
FIG. 3 illustrates a flowchart for high availability ECG access used in accordance with a preferred embodiment of the present invention.

FIG. 3 illustrates a flowchart 300 for a high availability ECG access used in accordance with a preferred embodiment of the present invention. An ECG or other waveform data may be stored at the remote, high availability database server cluster as described above in reference to FIG. 2. Later, at step 310, the database server cluster may be accessed to retrieve the ECG or other waveform. That is, a web browser, GE Medical Systems MUSE CV™ workstation graphical user interface, or other such information access device, for example, may be used to view the ECG or other waveform data via the web server or other user interface server of the database server cluster. For example, the patient returns to the hospital with chest pains, and a doctor wishes to review the patient's stored ECG to aid in the diagnosis and treatment of the patient. Thus, for example, the doctor uses a web browser on a personal computer to access the web server of the database server cluster.

Next, at step 320, access to the database server cluster may be authenticated as described above. For example, the doctor is prompted for a password at the web browser, and the password that the doctor enters is compared to a table of passwords. When the doctor's password is matched to an entry in the password table, for example, the doctor is allowed to access the database server cluster via the web server.

Then, at step 330, the user may request the ECG or other waveform data, for example. For example, the doctor selects the link at the web server to the ECG file. Next, at step 340, the ECG or other waveform data is transferred to the web server from storage at the database server cluster. For example, the requested ECG of the patient is retrieved from the RAID drive and stored in the cache of the web server for viewing by the doctor.

Finally, at step 340, the ECG or other waveform data may be retrieved and viewed via the web browser, GE Medical Systems MUSE CV™ workstation graphical user interface, or other such information access device, for example. For example, the doctor may view the stored ECG of the patient at the web server via the web browser on the personal computer.

Thus, the preferred embodiments of the present invention provide a highly available remote management system for ECGs and other waveform data. The preferred embodiments provide a system that helps to ensure high availability through redundant connections and redundant data storage. That is, the preferred embodiments help to ensure waveform data is always available through two redundant data storage devices and multiple access interfaces, for example.

The preferred embodiments provide a redundant system to help ensure access to ECG and other waveform data. Additionally, the preferred embodiments provide redundant components to help ensure reliable storage of ECG and other waveform data. The preferred embodiments also provide centralized remote access to allow a plurality of users to reliably store and access data. The preferred embodiments reduce computing and backup resources at healthcare facilities and improve the workflow of healthcare facilities in storing and retrieving ECG and other waveform data.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A centralized remote medical data management system, said system comprising:
   a primary remotely accessible centralized data storage storing medical data, wherein said medical data comprises at least electrocardiogram (ECG) data and wherein said medical data is collected from at least one medical device and is stored and managed at a location remote from where said medical data is collected;
   a redundant remotely accessible centralized data storage storing a redundant copy of said medical data;
   primary and redundant medical device connections connecting said at least one medical device to said primary remotely accessible centralized data storage and said redundant remotely accessible centralized data storage to collect said medical data from said at least one medical device; and
   primary and redundant user interfaces accessing said medical data at said primary remotely accessible centralized data storage and said redundant remotely accessible centralized data storage, said access including providing said at least ECG data for at least one of viewing and processing.

2. The system of claim 1, further comprising a data server for storing said medical data at said remotely accessible centralized data storage.

3. The system of claim 1, wherein said data server is capable of storing said medical data at said remotely accessible centralized data storage.

4. The system of claim 1, wherein said primary and redundant user interfaces comprise at least one web server.

5. The system of claim 1, wherein said primary and redundant user interfaces comprise at least one modem.

6. The system of claim 1, further comprising a web browser for accessing said medical data.

7. The system of claim 1, further comprising a workstation for accessing said medical data.

8. The system of claim 1, wherein said at least one medical device comprises an electrocardiograph capable of recording electrocardiogram data.

9. The system of claim 1, further comprising an authentication unit for authenticating access to said centralized remote medical data management system.

10. The system of claim 1, wherein said medical data comprises at least one of waveform data, measurements, and interpretations of signal data.

11. A method for remotely storing medical data, said method comprising:
receiving said medical data at a remotely accessible centralized data storage via a primary medical device connection, wherein a redundant medical device connection is used to store said medical data upon a failure of said primary medical device connection, said medical data comprising at least electrocardiogram (EGG) data;
storing said medical data at said remotely accessible centralized data storage, wherein said medical data is collected from at least one medical device and is stored and managed at a location remote from where said medical data is collected; and
storing said medical data in a redundant remotely accessible centralized data storage,
wherein said medical data is stored in said remotely accessible centralized data storage and said redundant remotely accessible centralized data storage for at least one of later viewing and processing of said at least ECG data.

12. The method of claim 11, further comprising the step of authenticating access to said remotely accessible centralized data storage.

13. The method of claim 11, wherein said storing step further comprises storing said medical data in said remotely accessible centralized data storage using a remote data server.

14. The method of claim 11, further comprising the step of retrieving said medical data from said remotely accessible centralized data storage.

15. The method of claim 14, wherein said retrieving step further comprises retrieving said medical data from said remotely accessible centralized data storage using a data server.

16. The method of claim 14, further comprising the step of displaying said medical data.

17. The method of claim 11, wherein said medical data comprises at least one of waveform data, measurements, and interpretations of signal data.

18. A centralized remote medical data access system, said system comprising:
a centralized remote data storage storing said medical data, wherein said medical data comprises at least electrocardiogram (EGG) data, said centralized remote data storage comprising a primary data storage and a redundant data storage;
a primary interface for externally transmitting said medical data from said centralized remote data storage; and
a redundant interface for externally transmitting said medical data from said centralized remote data storage,
wherein said primary interface and said redundant interface externally transmit said medical data from said centralized remote data storage for at least one of viewing and processing of said at least ECG data.

19. The system of claim 18, further comprising a data server retrieving said medical data from said centralized remote data storage.

20. The system of claim 19, wherein said data server is capable of retrieving said medical data from said redundant data storage.

21. The system of claim 18, wherein said primary interface comprises at least one web server.

22. The system of claim 18, wherein said primary interface comprises at least one modem.

23. The system of claim 18, further comprising an authentication unit for authenticating access to said centralized remote medical data access system.

24. The system of claim 18, further comprising a web browser for accessing said medical data.

25. The system of claim 18, further comprising a workstation for accessing said medical data.

26. The system of claim 18, further comprising an interface for receiving said medical data at said centralized remote medical data storage.

27. A method for reliably accessing medical data, said method comprising:
accessing a remote centralized medical data management system using a user interface, wherein said user interface comprises a primary interface and a redundant interface;
requesting desired medical data from said remote centralized medical data management system, wherein said medical data comprises at least electrocardiogram (ECG) data; and
retrieving said desired medical data from a data storage located at said remote centralized medical data management system for at least one of viewing and processing said at least ECG data, said data storage comprises a primary data storage and a redundant data storage storing primary and redundant medical data received from a primary medical device connection and a redundant medical device connection.

28. The method of claim 27, wherein said remote centralized medical data management system comprises a remote centralized redundant medical data management system.

29. The method of claim 27, further comprising the step of authenticating access to said remote centralized medical data management system.

30. The method of claim 27, wherein said retrieving step further comprises retrieving said desired medical data from said data storage using a data server.

31. The method of claim 27, further comprising the step of displaying said medical data.

32. The method of claim 27, further comprising the step of storing said medical data in said data storage.

33. The method of claim 32, wherein said storing step further comprises storing said medical data in said data storage using a remote data server.

34. The method of claim 27, wherein said medical data comprises at least one of waveform data, demographic data, measurements, and interpretations of signal data.

35. The method of claim 27, wherein said user interface is located on at least one web server.

36. A high availability remote data management system, said system comprising:
a data source transmitting medical data, wherein said medical data comprises at least electrocardiogram (ECG) data;
a medical device interface for receiving said medical data from said data source and transmitting said medical data to a primary data server, wherein said medical device interface comprises a primary medical device interface and a redundant medical device interface;
a primary data server receiving said medical data and storing said medical data in a primary remote centralized data storage;

a primary remote centralized data storage storing said medical data; and a redundant remote centralized data storage storing a redundant copy of said medical data, wherein said primary remote centralized data storage and said redundant remote centralized data storage store said medical data and said redundant copy of said medical data for at least one of viewing and processing of said at least ECG data.

37. The system of claim 36, further comprising a redundant data server receiving said medical data and storing said medical data in said redundant remote centralized data storage.

38. The system of claim 36, wherein said primary data server further stores said medical data at said redundant remote centralized data storage.

39. The system of claim 37, wherein said redundant data server further stores said medical data at said primary remote centralized data storage.

40. The system of claim 36, wherein said data source comprises an electrocardiogram unit for generating electrocardiogram data.

41. The system of claim 36, wherein said medical data comprises at least one of waveform data, demographic data, measurements, and interpretations of signal data.

42. The system of claim 36, further comprising an authentication unit for authenticating access to said high availability remote data management system.

43. The system of claim 36, further comprising a primary user interface and a redundant user interface for user access to said high availability remote data management system.

* * * * *